US007922777B2

(12) United States Patent
Hercouet et al.

(10) Patent No.: US 7,922,777 B2
(45) Date of Patent: Apr. 12, 2011

(54) LIGHTENING AND DYEING OF HUMAN KERATIN FIBERS USING AN ANHYDROUS COMPOSITION COMPRISING A MONOETHYANOLAMINE/BASIC AMINO ACID MIXTURE, AND DEVICE THEREFOR

(75) Inventors: Leïla Hercouet, Neuilly Plaisance (FR); Alain Lagrange, Coupvray (FR); Frédéric Simonet, Clichy (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 12/642,637

(22) Filed: Dec. 18, 2009

(65) Prior Publication Data

US 2010/0199441 A1    Aug. 12, 2010

Related U.S. Application Data

(60) Provisional application No. 61/147,208, filed on Jan. 26, 2009, provisional application No. 61/147,841, filed on Jan. 28, 2009, provisional application No. 61/149,104, filed on Feb. 2, 2009.

(30) Foreign Application Priority Data

Dec. 19, 2008 (FR) ...................................... 08 07315
Dec. 19, 2008 (FR) ...................................... 08 07316

(51) Int. Cl.
*A61Q 5/10* (2006.01)
(52) U.S. Cl. ............. 8/405; 8/406; 8/407; 8/426; 8/431; 8/462; 8/463; 8/602; 8/604; 8/111; 132/202; 132/208
(58) Field of Classification Search ............... 8/405, 406, 8/407, 426, 431, 462, 463, 602, 604, 111; 132/202, 208
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,845,293 A | 7/1989 | Junino et al. | |
| 5,021,066 A | 6/1991 | Aeby et al. | |
| 5,259,849 A * | 11/1993 | Grollier et al. | ..................... 8/405 |
| 5,364,414 A | 11/1994 | Lang et al. | |
| 5,817,155 A | 10/1998 | Yasuda et al. | |
| 6,010,541 A | 1/2000 | De La Mettrie | |
| 6,074,439 A | 6/2000 | De La Mettrie et al. | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 | 11/2003 | Vidal et al. | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,651,536 B2 | 1/2010 | Cottard et al. | |
| 7,766,977 B2 | 8/2010 | Cottard et al. | |
| 2003/0190297 A1 | 10/2003 | Narasimhan et al. | |
| 2003/0226217 A1 | 12/2003 | Bowes et al. | |
| 2004/0103488 A1 | 6/2004 | Yamashita et al. | |
| 2004/0105830 A1 | 6/2004 | Boswell et al. | |

(Continued)

FOREIGN PATENT DOCUMENTS

CA          1 268 421         5/1990

(Continued)

OTHER PUBLICATIONS

French Search Report for FR 0807315, dated Nov. 11, 2009.

(Continued)

*Primary Examiner* — Eisa B Elhilo
(74) *Attorney, Agent, or Firm* — Finnegan, Henderson, Farabow, Garrett & Dunner

(57) ABSTRACT

The present disclosure relates to a process for lightening human keratin fibers using at least one anhydrous composition (A) comprising at least one fatty substance, at least one surfactant, monoethanolamine and at least one basic amino acid, and at least one composition (B) comprising at least one oxidizing agent. The disclosure relates to a multi-compartment device comprising the abovementioned compositions (A) and (B).

26 Claims, No Drawings

U.S. PATENT DOCUMENTS

| | | |
|---|---|---|
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 A1 | 9/1988 |
| DE | 43 09 509 | 9/1994 |
| DE | 195 27 121 A1 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 A1 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 A1 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 A2 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 A1 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 A | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 A1 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2009/080667 | 7/2009 |

| | | | |
|---|---|---|---|
| WO | WO 2009/080668 | 7/2009 | |
| WO | WO 2009/080669 | 7/2009 | |
| WO | WO 2009/080670 | 7/2009 | |

OTHER PUBLICATIONS

French Search Report for FR 0807316, dated Nov. 18, 2009.
European Search Report for EP 09 17 9914, dated Mar. 25, 2010.
English language abstract of DE 195 27 121 A1, Jan. 30, 1997.
English language abstract of DE 10 2005 059 647 A1, Jun. 14, 2007.
English language abstract of FR 2 925 304 A1, Jun. 26, 2009.
English language abstract of JP 2004-262886, Sep. 24, 2004.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2007/006418, dated Jan. 18, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.

International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

LIGHTENING AND DYEING OF HUMAN KERATIN FIBERS USING AN ANHYDROUS COMPOSITION COMPRISING A MONOETHYANOLAMINE/BASIC AMINO ACID MIXTURE, AND DEVICE THEREFOR

This application claims benefit of U.S. Provisional Application Nos. 61/147,208, filed Jan. 26, 2009, 61/147,841, filed Jan. 28, 2009, and 61/149,104, filed Feb. 2, 2009. This application also claims benefit of priority under 35 U.S.C. §119 to French Patent Application Nos. 0807315 an 0807316, filed Dec. 19, 2008.

The present disclosure relates to a process for lightening or dyeing human keratin fibers using an at least one anhydrous composition (A) comprising at least one fatty substance, at least one surfactant, monoethanolamine and at least one basic amino acid, optionally an at least one composition (C1) comprising at least one oxidation dye and/or direct dye, and an at least one composition (B) comprising at least one oxidizing agent.

The disclosure relates to a multi-compartment device comprising the abovementioned compositions (A) and (B) and optionally (C1).

Processes for lightening human keratin fibers consist in employing an aqueous composition comprising at least one oxidizing agent, under alkaline pH conditions in the vast majority of cases. The role of this oxidizing agent is to degrade the melanin of the hair, which, depending on the nature of the oxidizing agent present, may lead to more or less pronounced lightening of the fibers. Thus, for relatively weak lightening, the oxidizing agent is generally hydrogen peroxide. When greater lightening is sought, peroxygenated salts, for instance persulfates, are usually used in the presence of hydrogen peroxide.

Among the methods for dyeing human keratin fibers, such as the hair, mention may be made of oxidation dyeing or permanent dyeing. For example, this dyeing method uses at least one oxidation dye precursor, usually at least one oxidation base optionally combined with at least one coupler.

In general, oxidation bases are chosen from ortho- or para-phenylenediamines, ortho- or para-aminophenols and heterocyclic compounds. These oxidation bases are colorless or weakly colored compounds, which, when combined with oxidizing products, can give access to colored species via a process of oxidative condensation.

The shades obtained with these oxidation bases are often varied by combining them with at least one coupler, these couplers being chosen from aromatic meta-diamines, meta-aminophenols, meta-diphenols and certain heterocyclic compounds, such as indole compounds.

The variety of molecules used as oxidation bases and couplers allows a wide range of colors to be obtained.

Direct dyeing or semi-permanent dyeing is also known. The process conventionally used in direct dyeing may consist in applying to the keratin fibers direct dyes, which are colored and coloring molecules that have affinity for the fibers, in leaving them on for a time to allow the molecules to penetrate, by diffusion, into the fiber, and then in rinsing them off.

The direct dyes generally used are chosen from nitrobenzene, anthraquinone, nitropyridine, azo, methine, azomethine, xanthene, acridine, azine, and triarylmethane direct dyes.

This type of process does not require the use of an oxidizing agent to develop the coloration. However, it is not excluded to use one in order to obtain, along with the coloration, a lightening effect. Such a process is then referred to as direct dyeing or semi-permanent dyeing under lightening conditions.

Processes of permanent or semi-permanent dyeing under lightening conditions thus consist in using, along with the dye composition, an aqueous composition comprising at least one oxidizing agent, under alkaline pH conditions in the vast majority of cases. The role of this oxidizing agent is to degrade the melanin of the hair, which, depending on the nature of the oxidizing agent present, leads to more or less pronounced lightening of the fibers. Thus, for relatively weak lightening, the oxidizing agent is generally hydrogen peroxide. When greater lightening is desired, peroxygenated salts, for instance persulfates, are usually used in the presence of hydrogen peroxide.

One of the difficulties arises from the fact that the lightening process or the processes of oxidation dyeing or direct dyeing under lightening conditions are performed under alkaline conditions and that the alkaline agent most commonly used is aqueous ammonia. The reason that aqueous ammonia may be useful for this is that it allows the pH of the composition to be adjusted to an alkaline pH to enable degradation of the oxidizing agent. However, this agent also causes swelling of the keratin fiber, with opening of the scales, which may promote the penetration of the oxidizing agent, and also of the dyes, essentially the oxidation dyes, into the fiber, and thus increases the efficacy of the reaction.

However, this basifying agent may be very volatile, which users find disagreeable due to the characteristic strong, rather unpleasant odor of ammonia that is given off during the process.

Furthermore, the amount of ammonia given off requires the use of higher contents than necessary in order to compensate for this loss. This is not without consequences on the user, who not only remains inconvenienced by the odor, but may also be confronted with greater risks of intolerance, for instance irritation of the scalp (stinging).

As regards the option of purely and simply replacing all or some of the aqueous ammonia with at least one other standard basifying agent, this does not lead to compositions that are as efficient as those based on aqueous ammonia, since these basifying agents may not afford sufficient lightening of pigmented fibers in the presence of the oxidizing agent.

One of the objects of the present disclosure is to propose processes for lightening human keratin fibers, which do not have the drawbacks of the processes performed with the existing compositions, these drawbacks being caused by the presence of large amounts of ammonia, but which remain at least as effective in terms of the lightening and the uniformity of lightening.

One of the objects of the present disclosure is also to propose processes for dyeing human keratin fibers, performed in the presence of an oxidizing agent, which do not have the drawbacks of the processes performed with the existing compositions, these drawbacks arising from the presence of large amounts of ammonia, but which remain at least as effective in terms of the strength of the coloration obtained, the chromaticity and the uniformity of dyeing along the fiber.

These aims and others can be achieved by the present disclosure, one subject of which is a process for lightening human keratin fibers comprising applying to the human keratin fibers:

a) at least one anhydrous composition (A) comprising at least one fatty substance, at least one surfactant, monoethanolamine and at least one basic amino acid; and b) at least one composition (B) comprising at least one oxidizing agent.

Another subject of the disclosure concerns a process for dyeing human keratin fibers comprising applying to the human keratin fibers:

a) at least one anhydrous composition (A) comprising at least one fatty substance, at least one surfactant, monoethanolamine and at least one basic amino acid, and b) at least one composition (C1) comprising at least one oxidation dye and/or direct dye;

c) at least one aqueous composition (B) comprising at least one oxidizing agent.

The disclosure also relates to a multi-compartment device comprising the abovementioned compositions (A) and (B) and optionally (C1).

Other characteristics and advantages of the disclosure will emerge more clearly on reading the description and the examples that follow.

In the text hereinbelow, unless otherwise indicated, the limits of a range of values are included in that range.

The human keratin fibers treated via the process according to the disclosure may be hair.

The anhydrous cosmetic composition (A) may have a water content equal to 0 or less than 5% by weight, such as less than 2% by weight or less than 1% by weight, relative to the weight of the said composition. It should be noted that the water may also be in the form of bound water, such as the water of crystallization of salts or traces of water absorbed by the starting materials used in the preparation of the compositions according to the disclosure.

In addition, when the process according to the disclosure is a lightening process, this process is performed in the presence of compositions not comprising any direct dye or oxidation dye precursor (bases and couplers) usually used for the dyeing of human keratin fibers, or else, if it does comprise any, their total content does not exceed 0.005% by weight relative to the weight of the anhydrous composition and of the aqueous composition comprising the oxidizing agent. Specifically, at such a content, only the composition would possibly be dyed, i.e. no dyeing effect would be observed on the keratin fibers.

The process may be performed without oxidation base, or coupler or direct dye.

As has been mentioned, the anhydrous cosmetic composition (A) comprises at least one fatty substance.

The term "fatty substance" means an organic compound that is insoluble in water at ordinary temperature (25° C.) and at atmospheric pressure (760 mmHg) (solubility of less than 5%, such as 1% or 0.1%). They comprise in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

According to the disclosure, the fatty substances are chosen from compounds that are liquid or pasty at room temperature and at atmospheric pressure.

The fatty substances may be chosen from $C_6$-$C_{16}$ lower alkanes, non-silicone oils of animal, plant, mineral or synthetic origin, fatty alcohols, fatty acids, esters of a fatty acid and/or of a fatty alcohol, non-silicone waxes, and silicones.

It is recalled that, for the purposes of the disclosure, the fatty alcohols, fatty esters and fatty acids may comprise at least one linear or branched, saturated or unsaturated hydrocarbon-based group comprising 6 to 30 carbon atoms, which is optionally substituted, for example with at least one hydroxyl group (such as 1 to 4). If they are unsaturated, these compounds may comprise one to three conjugated or non-conjugated carbon-carbon double bonds.

As regards the $C_6$-$C_{16}$ lower alkanes, they may be linear, branched, or cyclic. Examples that may be mentioned include hexane, undecane, dodecane, tridecane, and isoparaffins such as isohexadecane, and isodecane.

As oils of animal, plant, mineral or synthetic origin that may be used in the composition of the disclosure, examples that may be mentioned include:

hydrocarbon-based oils of animal origin, such as perhydrosqualene;

triglyceride oils of plant or synthetic origin, such as liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, sunflower oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, of more than 16 carbon atoms, such as volatile or non-volatile liquid paraffins, and derivatives thereof, petroleum jelly, liquid petroleum jelly, polydecenes, hydrogenated polyisobutenes such as PARLEAM®; such as liquid paraffins, petroleum jelly, liquid petroleum jelly, polydecenes and hydrogenated polyisobutenes such as PARLEAM®;

fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the disclosure may chosen from saturated or unsaturated, linear or branched alcohols comprising from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol, or linoleyl alcohol.

The fatty acids that may be used in the context of the disclosure may be chosen from saturated or unsaturated carboxylic acids comprising from 6 to 30 carbon atoms such as from 9 to 30 carbon atoms. They may be chosen from myristic acid, palmitic acid, stearic acid, behenic acid, oleic acid, linoleic acid, linolenic acid and isostearic acid.

As regards the esters of a fatty acid and/or of a fatty alcohol, which may be different from the triglycerides mentioned above; mention may be made of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate;

isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still in the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is possible to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ such as $C_{12}$-$C_{22}$ fatty acids. It is recalled that the term "sugar" means oxygen-bearing hydrocarbon-based compounds comprising several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose and lactose, and derivatives thereof, alkyl derivatives, such as methyl derivatives, for instance methylglucose.

The sugar esters of fatty acids may be chosen from the group comprising the esters or mixtures of esters of sugars described previously and of linear or branched, saturated or unsaturated $C_6$-$C_{30}$ such as $C_{12}$-$C_{22}$ fatty acids. If they are unsaturated, these compounds may comprise one to three conjugated or nonconjugated carbon-carbon double bonds.

The esters according to this variant may also be chosen from mono-, di-, tri-, tetraesters and polyesters, and mixtures thereof.

These esters may be chosen, for example from oleates, laurates, palmitates, myristates, behenates, cocoates, stearates, linoleates, linolenates, caprates and arachidonates, or mixtures thereof such as, oleo-palmitate, oleo-stearate and palmito-stearate mixed esters.

It is possible to use monoesters and diesters, such as sucrose, glucose or methylglucose mono- or dioleates, stearates, behenates, oleopalmitates, linoleates, linolenates and oleostearates.

An example that may be mentioned is the product sold under the name GLUCATE® DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% ditriester-polyester;

the sucrose mono-dipalmito-stearate sold by the company Goldschmidt under the name TEGOSOFT® PSE.

The at least one non-silicone wax may be chosen from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the disclosure are for example marine waxes such as the product sold by the company Sophim under the reference M82, and polyethylene waxes or waxes of polyolefins in general.

The silicones that may be used in the cosmetic compositions of the present disclosure are volatile or non-volatile, cyclic, linear or branched silicones, which are unmodified or modified with organic groups, having a viscosity from $5 \times 10^{-6}$ to 2.5 m²/s at 25° C., such as $1 \times 10^{-5}$ to 1 m²/s.

The silicones that may be used in accordance with the disclosure may be in the form of oils, waxes, resins or gums.

The silicone may be chosen from polydialkylsiloxanes, such as polydimethylsiloxanes (PDMS), and organomodified polysiloxanes comprising at least one functional group chosen from poly(oxyalkylene) groups, amino groups, and alkoxy groups.

Organopolysiloxanes are defined in greater detail in Walter Noll's "Chemistry and Technology of Silicones" (1968) Academic Press. They may be volatile or non-volatile.

When they are volatile, the silicones may be chosen from those having a boiling point of between 60° C. and 260° C., such as (i) cyclic polydialkylsiloxanes comprising from 3 to 7 such as 4 to 5 silicon atoms. These are, for example, octamethylcyclotetrasiloxane sold for example under the name VOLATILE SILICONE® 7207 by Union Carbide or SILIBIONE® 70045 V2 by Rhodia, decamethylcyclopentasiloxane sold under the name VOLATILE SILICONE® 7158 by Union Carbide, and SILIBIONE® 70045 V5 by Rhodia, and mixtures thereof.

Mention may also be made of cyclocopolymers of the dimethylsiloxane/methylalkylsiloxane type, such as VOLATILE SILICONE® FZ 3109 sold by the company Union Carbide, of formula:

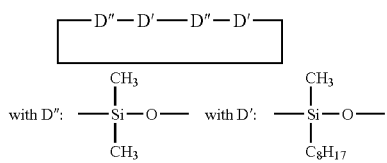

Mention may also be made of mixtures of cyclic polydialkylsiloxanes with organosilicon compounds, such as the mixture of octamethylcyclotetrasiloxane and tetra-trimethylsilylpentaerythritol (50/50) and the mixture of octamethylcyclotetrasiloxane and oxy-1,1'-bis(2,2,2',2',3,3'-hexatrimethylsilyloxy)neopentane.

Additional non-limiting examples of volatile silicones include (ii) linear volatile polydialkylsiloxanes comprising 2 to 9 silicon atoms and having a viscosity of less than or equal to $5\times10^{-6}$ m$^2$/s at 25° C. An example is decamethyltetrasiloxane sold for example under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Non-volatile polydialkylsiloxanes, polydialkylsiloxane gums and resins, polyorganosiloxanes modified with the above organofunctional groups, and mixtures thereof, may be used.

These silicones may be chosen from polydialkylsiloxanes, among which mention may be made of polydimethylsiloxanes comprising trimethylsilyl end groups. The viscosity of the silicones is measured, for example, at 25° C. according to ASTM standard 445 Appendix C.

Among these polydialkylsiloxanes, mention may be made, in a non-limiting manner, of the following commercial products:

the SILIBIONE® oils of the 47 and 70 047 series or the MIRASILI® oils sold by Rhodia, for instance the oil 70 047 V 500 000;

the oils of the MIRASILI® series sold by the company Rhodia;

the oils of the 200 series from the company Dow Corning, such as DC200 with a viscosity of 60 000 mm$^2$/s;

the VISCASILI® oils from General Electric and certain oils of the SF series (SF 96, SF 18) from General Electric.

Mention may also be made of polydimethylsiloxanes comprising dimethylsilanol end groups known under the name Dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt, which are poly($C_1$-$C_{20}$)dialkylsiloxanes.

The silicone gums that can be used in accordance with the disclosure are for example polydialkylsiloxanes such as polydimethylsiloxanes with high number-average molecular masses of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used in accordance with the disclosure are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, for example a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product may comprise 15% SE 30 gum and 85% SF 96 oil.

The organopolysiloxane resins that can be used in accordance with the disclosure are crosslinked siloxane systems comprising the following units:

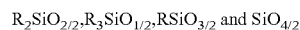

$R_2SiO_{2/2}, R_3SiO_{1/2}, RSiO_{3/2}$ and $SiO_{4/2}$ in which R represents an alkyl comprising 1 to 16 carbon atoms. Among these products, R may represent a $C_1$-$C_4$ lower alkyl radical, such as methyl.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of trimethyl siloxysilicate type resins sold, for example, under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based group.

Besides the silicones described above, the organomodified silicones may be polydiarylsiloxanes, such as polydiphenylsiloxanes, and polyalkylarylsiloxanes functionalized with the organofunctional groups mentioned previously.

The polyalkylarylsiloxanes may be chosen from linear and/or branched polydimethyl/methylphenylsiloxanes and polydimethyl/diphenylsiloxanes with a viscosity of from $1\times10^{-5}$ to $5\times10^{-2}$ m$^2$/s at 25° C.

Among these polyalkylarylsiloxanes, examples that may be mentioned include the products sold under the following names:

the SILIBIONE® oils of the 70 641 series from Rhodia;

the oils of the RHODORSIL® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, $C_1$-$C_4$ aminoalkyl groups;

alkoxylated groups such as the product sold under the name Silicone Copolymer F-755 by SWS Silicones, and ABIL WAX® 2428, 2434 and 2440 by the company Goldschmidt.

For example the fatty substances do not comprise any $C_2$-$C_3$ oxyalkylene units or any glycerolic units.

The fatty substances may be chosen from compounds that are liquid or pasty at room temperature and at atmospheric pressure.

The fatty substance may be a compound that is liquid at a temperature of 25° C. and at atmospheric pressure.

The fatty substances may be other than fatty acids.

The fatty substances may be chosen from $C_6$-$C_{16}$ lower alkanes, non-silicone oils of plant, mineral or synthetic origin, fatty alcohols, esters of a fatty acid and/or of a fatty alcohol, and silicones, or mixtures thereof; such as $C_6$-$C_{16}$ lower alkanes, non-silicone oils of plant, mineral or synthetic origin, fatty alcohols, and esters of a fatty acid and/or of a fatty alcohol, or mixtures thereof.

The fatty substance may be chosen from liquid petroleum jelly, polydecenes, and liquid esters of a fatty acid and/or of a fatty alcohol, or mixtures thereof.

The anhydrous cosmetic composition has a fatty substance content ranging from 10% to 99% by weight, such as ranging from 20% to 90% by weight or ranging from 25% to 80% by weight relative to the weight of the anhydrous composition.

The anhydrous cosmetic composition (A) also comprises at least one surfactant.

The surfactant may be chosen from nonionic surfactants and anionic surfactants.

The anionic surfactants may be chosen from the salts (such as alkali metal salts, for example sodium salts, ammonium salts, amine salts, amino alcohol salts or alkaline-earth metal salts such as magnesium salts) of the following compounds:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates; alkylsulfosuccinates;

alkylsulfoacetates;

acylsarcosinates; acylisethionates and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, such as those comprising from 2 to 50 ethylene oxide groups;

and mixtures thereof.

It should be noted that the alkyl or acyl radical of these various compounds may comprise from 6 to 24 carbon atoms such as from 8 to 24 carbon atoms, and the aryl radical may represent a phenyl or benzyl group.

The nonionic surfactants may be chosen from monooxyalkylenated or polyoxyalkylenated, monoglycerolated or polyglycerolated nonionic surfactants. The oxyalkylene units may be oxyethylene or oxypropylene units, or a combination thereof, for example oxyethylene units.

Examples of oxyalkylenated nonionic surfactants that may be mentioned include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, condensates of ethylene oxide and/or of propylene oxide, inter alia, alone or as mixtures.

The surfactants comprise a number of moles of ethylene oxide and/or of propylene oxide ranging from 1 to 100 such as ranging from 2 to 50. For example, the nonionic surfactants do not comprise any oxypropylene units.

In accordance with one embodiment of the disclosure, the oxyalkylenated nonionic surfactants are chosen from oxyethylenated $C_8$-$C_{30}$ alcohols comprising from 1 to 100 mol of ethylene oxide, and polyoxyethylenated esters of saturated or unsaturated, linear or branched $C_8$-$C_{30}$ acids, and of sorbitol, comprising from 1 to 100 mol of ethylene oxide.

As examples of monoglycerolated or polyglycerolated nonionic surfactants, monoglycerolated or polyglycerolated $C_8$-$C_{40}$ alcohols may be used.

The monoglycerolated or polyglycerolated $C_8$-$C_{40}$ alcohols may correspond to the following formula:

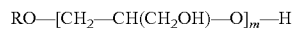

in which R represents a linear or branched $C_8$-$C_{40}$ such as $C_8$-$C_{30}$ alkyl or alkenyl radical, and m represents a number ranging from 1 to 30 such as from 1 to 10.

As examples of compounds that are suitable in the context of the disclosure, mention may be made of lauryl alcohol comprising 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is possible to use the $C_8/C_{10}$ alcohol comprising 1 mol of glycerol, the $C_{10}/C_{12}$ alcohol comprising 1 mol of glycerol and the $C_{12}$ alcohol comprising 1.5 mol of glycerol.

The surfactant may be present in the anhydrous composition is a nonionic surfactant.

The surfactant content in the anhydrous composition may ranging from 0.1% to 50% by weight such as ranging from 0.5% to 30% by weight relative to the weight of the anhydrous composition.

Composition (A) furthermore comprises monoethanolamine, and at least one basic amino acid.

The basic amino acids that may be used in the context of the disclosure may be chosen from those comprising an additional amine function optionally included in a ring or a ureido function.

Such basic amino acids may be chosen from those corresponding to formula (I) below:

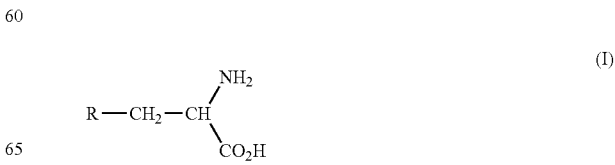

which R represents a group chosen from:

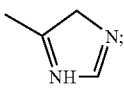

—(CH$_2$)$_3$NH$_2$;
—(CH$_2$)$_2$NH$_2$;
—(CH$_2$)$_2$NHCONH$_2$; and

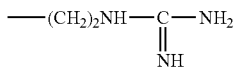

The compounds corresponding to formula (I) are histidine, lysine, arginine, ornithine and citrulline, such as arginine, lysine and histidine, or mixtures thereof.

Composition (A) may have a monoethanolamine content ranging from 0.1% to 40% by weight, such as ranging from 0.5% to 20% by weight, relative to the weight of the said composition.

As regards the content of the at least one basic amino acid, this may range from 0.1% to 40% by weight, such as ranging from 0.5% to 20% by weight, relative to the weight of the said composition.

It should be noted that, according to one embodiment, the monoethanolamine/basic amino acid weight ratio may range from 0.1 to 10, such as from 0.3 to 10 or from 1 to 5.

The cosmetic composition (A) may also comprise various adjuvants conventionally used in hair dyeing compositions, such as anionic, cationic, nonionic, amphoteric or zwitterionic polymers or mixtures thereof; mineral thickeners, fillers such as clays, talc; organic thickeners with, such as, anionic, cationic, nonionic and amphoteric polymeric associative thickeners; antioxidants; penetrants; sequestrants; fragrances; dispersants; film-forming agents; ceramides; conditioning agents; preserving agents; opacifiers.

The above adjuvants are generally present in an amount for each of them of between 0.01% and 20% by weight relative to the weight of composition (A).

The composition may comprise at least one mineral thickener chosen from organophilic clays, fumed silicas, and mixtures thereof.

The organophilic clay may be chosen from montmorillonite, bentonite, hectorite, attapulgite, sepiolite, and mixtures thereof. The clay may be a bentonite or a hectorite.

These clays may be modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst, and Claytone AF and Claytone APA by the company Southern Clay; quaternium-18/benzalkonium bentonites such as those sold under the names Claytone HT and Claytone PS by the company Southern Clay; quaternium-18 hectorites such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by the company Rheox, and Simagel M and Simagel SI 345 by the company Biophil.

The fumed silicas may be obtained by high-temperature hydrolysis of a volatile silicon compound in an oxhydric flame, producing a finely divided silica. This process makes it possible to obtain hydrophilic silicas having a large number of silanol groups at their surface. Such hydrophilic silicas are sold, for example, under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of the silica, via a chemical reaction generating a reduction in the number of silanol groups. It is possible to substitute silanol groups with hydrophobic groups: a hydrophobic silica is then obtained.

The hydrophobic groups may be chosen from:
trimethylsiloxyl groups, which are obtained by treating fumed silica in the presence of hexamethyldisilazane. Silicas thus treated are known as "silica silylate" according to the CTFA (6th Edition, 1995). They are sold, for example, under the references AEROSIL R812® by the company Degussa and CAB-O-SIL TS-530® by the company Cabot; and
dimethylsilyloxyl or polydimethylsiloxane groups, which may be obtained by treating fumed silica in the presence of polydimethylsiloxane or dimethyldichlorosilane. Silicas thus treated are known as "silica dimethyl silylate" according to the CTFA (6th Edition, 1995). They are sold, for example, under the references AEROSIL R972® and AEROSIL 8974® by the company Degussa, and CAB-O-SIL TS-610® and CAB-O-SIL TS-720® by the company Cabot.

The fumed silica may have a particle size that may be nanometric to micrometric, for example ranging from about 5 to 200 nm.

The composition may comprise a hectorite, an organo-modified bentonite or an optionally modified fumed silica.

When it is present, the mineral thickener represents from 1% to 30% by weight relative to the weight of the composition.

The composition may also comprise at least one organic thickener.

These thickeners may be chosen from fatty acid amides (coconut monoethanolamide or diethanolamide, oxyethylenated alkyl ether carboxylic acid monoethanolamide), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl comprising at least 10 carbon atoms) that are capable, in an aqueous medium, of reversibly combining with each other or with other molecules).

According to one embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropanesulfonic acid crosslinked homopolymers, such as from cellulose-based thickeners such as with hydroxyethylcellulose.

The content of organic thickener(s), if they are present, usually ranges from 0.01% to 20% by weight, such as from 0.1% to 5% by weight, relative to the weight of the composition.

Composition (A) may be in the form of a gel or a cream.

When the process according to the disclosure is a dyeing process, it is performed in the presence of a composition (C1) comprising at least one oxidation dye and/or direct dye.

The oxidation dyes are generally chosen from at least one oxidation base optionally combined with at least one coupler.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be used.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diamino-phenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-β-hydroxyethyl-aminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)-amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyra-zolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof. 4,5-diamino-1-(β-methoxyethyl)pyrazole may also be used.

A 4,5-diaminopyrazole may be used, such as a 4,5-diamino-1-(β-hydroxyethyl)pyrazole and/or a salt thereof.

Pyrazole derivatives that may also be mentioned include diamino-N,N-dihydropyrazolopyrazolones and those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H, 5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6, 7-dihydro-1H,5H-pyrazolo[1,2-a]pyrazol-1-one 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof may be used.

Heterocyclic bases that may be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

The composition according to the disclosure may optionally comprise at least one coupler chosen from those conventionally used for the dyeing of keratin fibers.

Among these couplers, mention may be made of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-β-hydroxy-ethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2, 6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure may be chosen from the addition salts with an acid such as the hydrochlorides, hydrobromides, sulfates, citrates, succinates, tartrates, lactates, tosylates, benzenesulfonates, phosphates and acetates.

The at least one oxidation base may represent from 0.0001% to 10% by weight relative to the total weight of the composition, such as from 0.005% to 5% by weight, relative to the total weight of the composition.

The content of the at least one coupler, if it is present, may represents from 0.0001% to 10% by weight relative to the total weight of the composition, such as from 0.005% to 5% by weight relative to the total weight of the composition.

As regards the direct dyes, these dyes may be chosen from ionic and nonionic species, such as cationic or nonionic species.

Examples of suitable direct dyes that may be mentioned include the following direct dyes: azo dyes; methine dyes; carbonyl dyes; azine dyes; nitro (hetero)aryl dyes; tri(hetero) arylmethane dyes; porphyrin dyes; phthalocyanin dyes, and natural direct dyes, alone or as mixtures.

For example, the azo dyes comprise an —N═N— function, the two nitrogen atoms of which are not simultaneously engaged in a ring. However, it is not excluded for one of the two nitrogen atoms of the sequence —N═N— to be engaged in a ring.

The dyes of the methine family may be compounds comprising at least one sequence chosen from >C═C< and —N═C<, the two atoms of which are not simultaneously engaged in a ring. However, it is pointed out that one of the nitrogen or carbon atoms of the sequences may be engaged in a ring. The dyes of this family may be derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made of azine, xanthene, thioxanthene, fluorindine, acridine, (di)oxazine, (di)thiazine and pyronin.

The nitro (hetero)aromatic dyes may be nitrobenzene or nitropyridine direct dyes.

As regards the dyes of porphyrin or phthalocyanin type, it is possible to use cationic or non-cationic compounds, optionally comprising at least one metal or metal ion, for instance alkali metals, alkaline-earth metals, zinc and silicon.

Examples of suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone such as anthraquinone, naphthoquinone or benzoquinone direct dyes; azine; xanthene; triarylmethane; indoamine; indigoid; phthalocyanin and porphyrin direct dyes, and natural direct dyes, alone or as mixtures.

These dyes may be monochromophoric dyes (i.e. comprising only one dye) or polychromophoric, such as di- or trichromophoric; the chromophores possibly being identical or different, and from the same chemical family or otherwise. It should be noted that a polychromophoric dye comprises several radicals each derived from a molecule that absorbs in the visible region between 400 and 800 nm. Furthermore, this absorbance of the dye does not require any prior oxidation thereof, or combination with any other chemical species.

In the case of polychromophoric dyes, the chromophores are connected together by means of at least one linker, which may be cationic or non-cationic.

The linker may be a linear, branched or cyclic $C_1$-$C_{20}$ alkyl chain, optionally interrupted with at least one heteroatom (such as nitrogen or oxygen) and/or with at least one group comprising such an atom (CO, SO$_2$), optionally interrupted with at least one heterocycle that may or may not be fused to a phenyl nucleus and comprising at least one quaternized nitrogen atom engaged in the said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted C$_1$-C$_{15}$ alkyl groups; the linker not comprising any nitro, nitroso or peroxy groups.

If the heterocycles or aromatic nuclei are substituted, they are substituted, for example, with at least one C$_1$-C$_8$ alkyl radical optionally substituted with a hydroxyl, C$_1$-C$_2$ alkoxy, C$_2$-C$_4$ hydroxyalkoxy, acetylamino, or amino group substituted with one or two C$_1$-C$_4$ alkyl radicals, optionally bearing at least one hydroxyl group, or the two radicals possibly forming, with the nitrogen atom to which they are attached, a 5- or 6-membered heterocycle optionally comprising another heteroatom identical to or different from nitrogen; a halogen atom; a hydroxyl group; a C$_1$-C$_2$ alkoxy radical; a C$_2$-C$_4$ hydroxyalkoxy radical; an amino radical; an amino radical substituted with one or two identical or different C$_1$-C$_4$ alkyl radicals optionally bearing at least one hydroxyl group.

Among the benzenic direct dyes that may be used, mention may be made in a nonlimiting manner of the following compounds:
1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, methine and tetraazapentamethine direct dyes that may be used according to the disclosure, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Mention may be made of the following dyes of formulae (I) to (IV), such as the compounds of formulae (I) and (III):

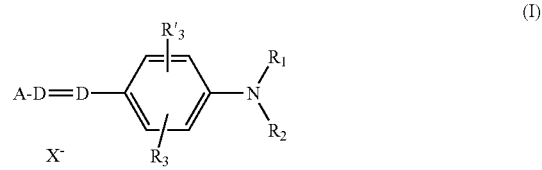

in which:

D represents a nitrogen atom or a —CH group,

R$_1$ and R$_2$, which may be identical or different, represent a hydrogen atom; a C$_1$-C$_4$ alkyl radical which may be substituted with a —CN, —OH or —NH$_2$ radical, or form, with a carbon atom of the benzene ring, a heterocycle optionally comprising oxygen or nitrogen, which may be substituted with at least one C$_1$-C$_4$ alkyl radical; a 4'-aminophenyl radical, R$_3$ and R'$_3$, which may be identical or different, represent a hydrogen atom or a halogen atom chosen from chlorine, bromine, iodine and fluorine, or a cyano, C$_1$-C$_4$ alkyl, C$_1$-C$_4$ alkoxy or acetyloxy radical, X$^-$ represents an anion which may chosen from chloride, methyl sulfate and acetate, A represents a group chosen from structures A$_1$ to A$_{18}$ below:

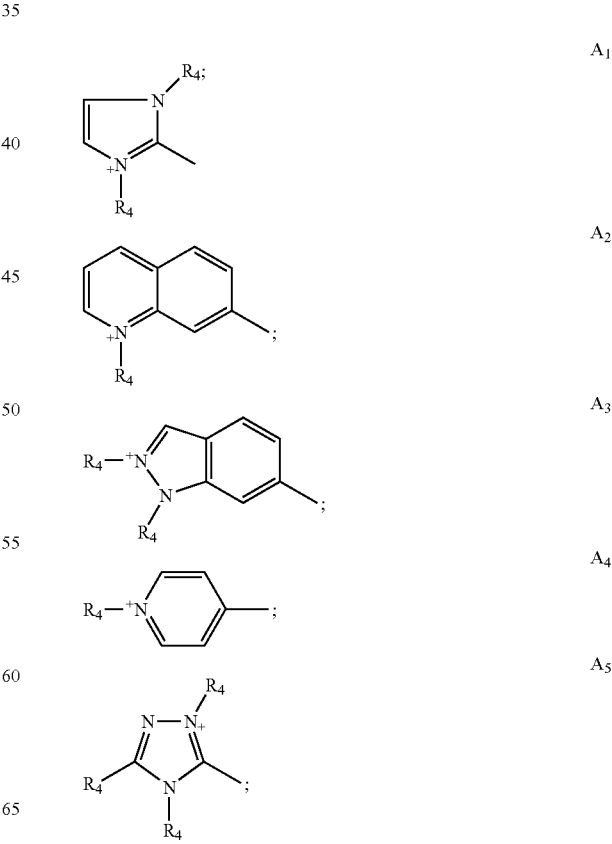

-continued

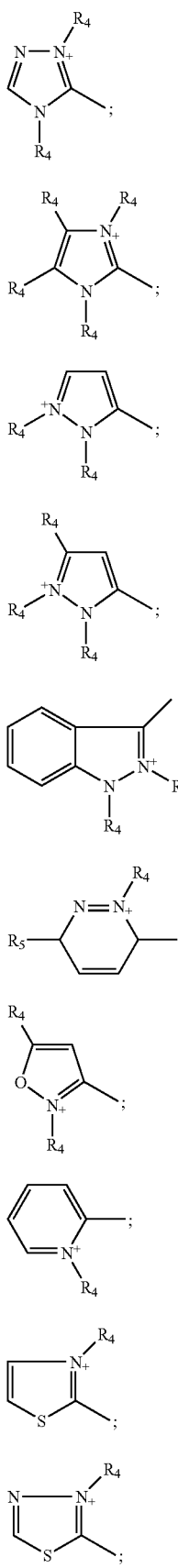

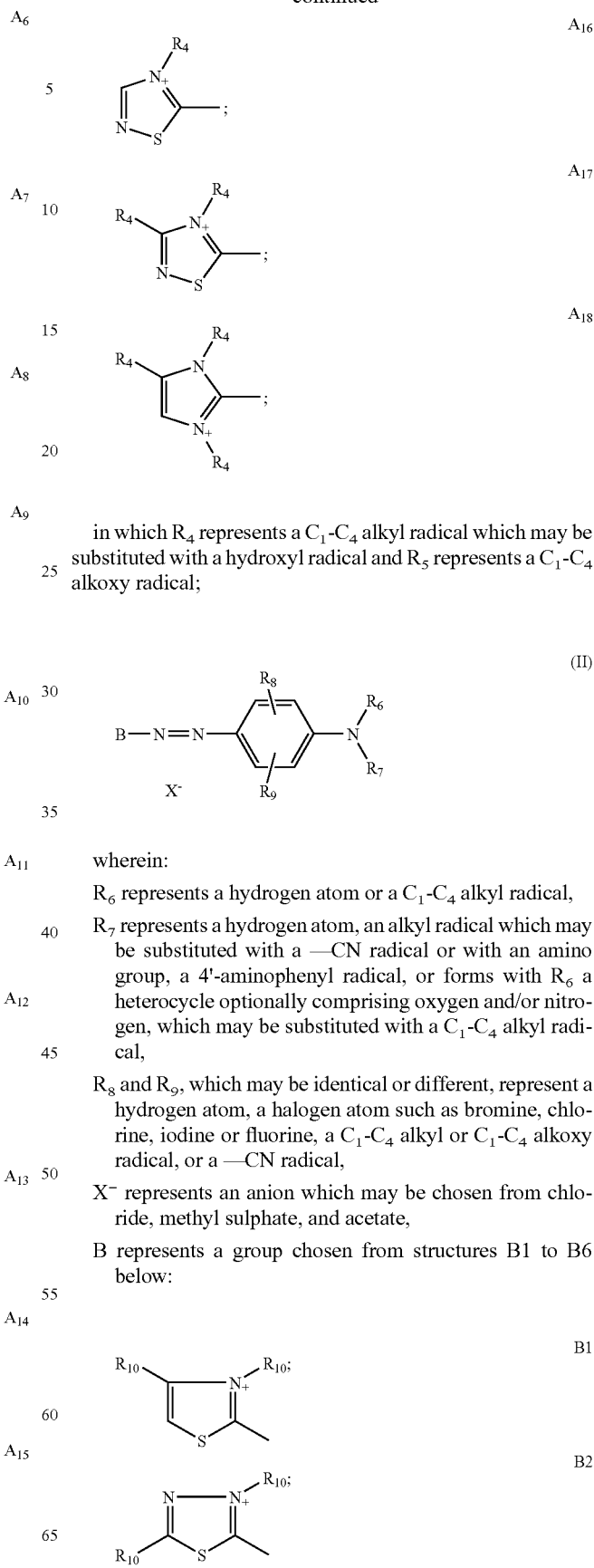

in which $R_4$ represents a $C_1$-$C_4$ alkyl radical which may be substituted with a hydroxyl radical and $R_5$ represents a $C_1$-$C_4$ alkoxy radical;

wherein:

$R_6$ represents a hydrogen atom or a $C_1$-$C_4$ alkyl radical, $R_7$ represents a hydrogen atom, an alkyl radical which may be substituted with a —CN radical or with an amino group, a 4'-aminophenyl radical, or forms with $R_6$ a heterocycle optionally comprising oxygen and/or nitrogen, which may be substituted with a $C_1$-$C_4$ alkyl radical, $R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical, or a —CN radical, $X^-$ represents an anion which may be chosen from chloride, methyl sulphate, and acetate, B represents a group chosen from structures B1 to B6 below:

-continued

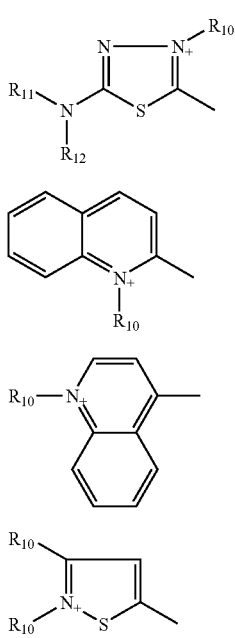

in which $R_{10}$ represents a $C_1$-$C_4$ alkyl radical, $R_{11}$ and $R_{12}$, which may be identical or different, represent a hydrogen atom or a $C_1$-$C_4$ alkyl radical;

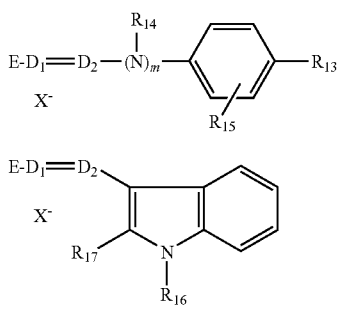

in which:
- $R_{13}$ represents a hydrogen atom, a $C_1$-$C_4$ alkoxy radical or a halogen atom such as bromine, chlorine, iodine, or fluorine,
- $R_{14}$ represents a hydrogen atom, a $C_1$-$C_4$ alkyl radical or forms, with a carbon atom of the benzene ring, a heterocycle optionally comprising oxygen and/or substituted with at least one $C_1$-$C_4$ alkyl group,
- $R_{15}$ represents a hydrogen atom or a halogen atom such as bromine, chlorine, iodine, or fluorine,
- $R_{16}$ and $R_{17}$, which may be identical or different, represent a hydrogen atom or a $C_1$-$C_4$ alkyl radical,
- $D_1$ and $D_2$, which may be identical or different, represent a hydrogen atom or a —CH group,
- m=0 or 1, such as 1,
- it being understood that when $R_{13}$ represents an unsubstituted amino group, then $D_1$ and $D_2$ simultaneously represent a —CH group and m=0,
- $X^-$ represents an anion which may be chosen from chloride, methyl sulphate, and acetate,
- E represents a group chosen from structures E1 to E8 below, such as E1, E2 and E7:

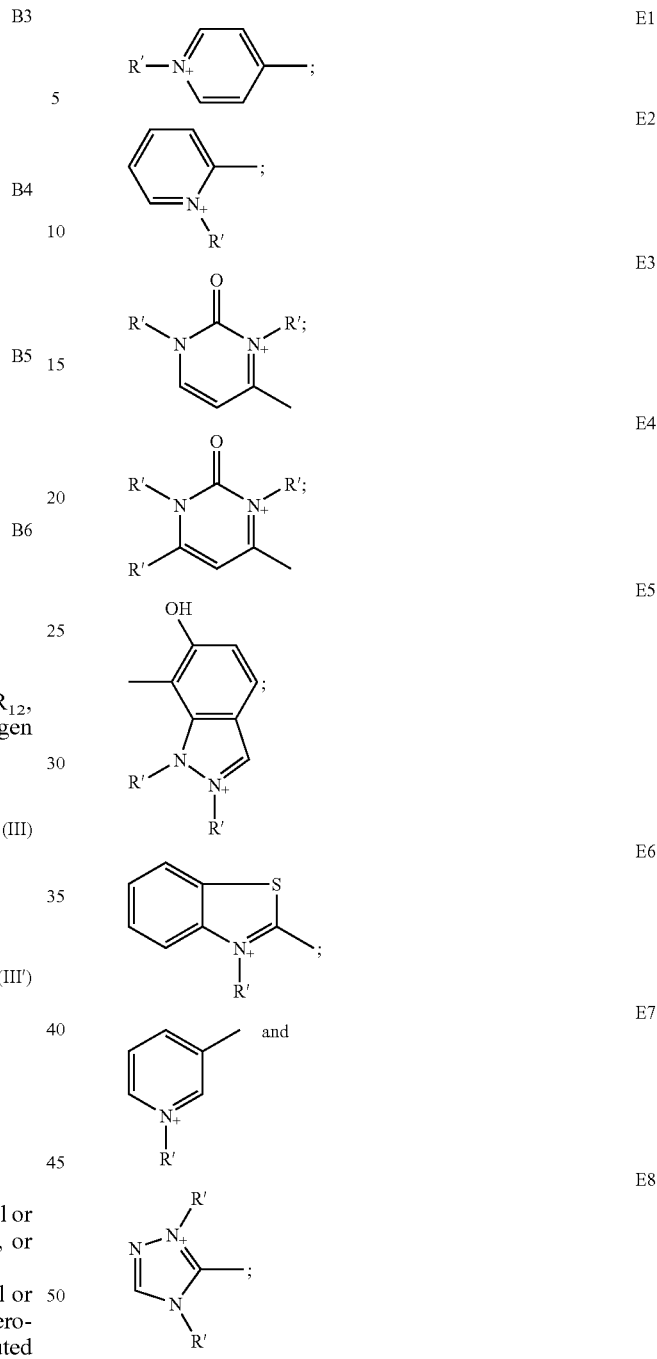

in which R' represents a $C_1$-$C_4$ alkyl radical;
when m=0 and $D_1$ represents a nitrogen atom, then E may also represent a group of structure E9 below:

n which R' represents a $C_1$-$C_4$ alkyl radical.

$$G-N=N-J \quad (IV)$$

in which:
the symbol G represents a group chosen from the structures $G_1$ to $G_3$ below:

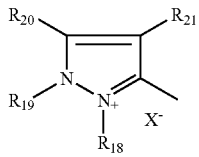

$G_1$

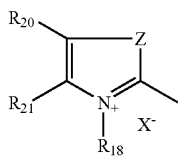

$G_2$

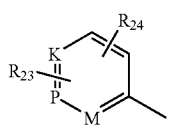

$G_3$ in which structures $G_1$ to $G_3$:
$R_{18}$ represents a $C_1$-$C_4$ alkyl radical, a phenyl radical which may be substituted with a $C_1$-$C_4$ alkyl radical, or a halogen atom chosen from chlorine, bromine, iodine and fluorine;
$R_{19}$ represents a $C_1$-$C_4$ alkyl radical or a phenyl radical;
$R_{20}$ and $R_{21}$, which may be identical or different, represent a $C_1$-$C_4$ alkyl radical, a phenyl radical, or form together in $G_1$ a benzene ring substituted with at least one $C_1$-$C_4$ alkyl, $C_1$-$C_4$ alkoxy or $NO_2$ radicals, or form together in $G_2$ a benzene ring optionally substituted with at least one $C_1$-$C_4$ alkyl, $C_1$-$C_4$ alkoxy or $NO_2$ radicals;
$R_{20}$ may also represent a hydrogen atom;
Z represents an oxygen or sulfur atom or a group —$NR_{19}$;
M represents a group —CH, —CR(R denoting $C_1$-$C_4$ alkyl) or —$NR_{22}(X^-)_r$;
K represents a group —CH, —CR(R denoting $C_1$-$C_4$ alkyl) or —$NR_{22}(X^-)_r$;
P represents a group —CH, —CR(R denoting $C_1$-$C_4$ alkyl) or —$NR_{22}(X^-)_r$;
r represents 0 or 1;
$R_{22}$ represents an $O^-$ atom, a $C_1$-$C_4$ alkoxy radical or a $C_1$-$C_4$ alkyl radical;
$R_{23}$ and $R_{24}$, which may be identical or different, represent a hydrogen atom or a halogen atom chosen from chlorine, bromine, iodine, and fluorine, a $C_1$-$C_4$ alkyl or $C_1$-$C_4$ alkoxy radical, or an —$NO_2$ radical;
$X^-$ represents an anion which may be chosen from chloride, iodide, methyl sulfate, ethyl sulfate, acetate, and perchlorate;
with the proviso that,
if $R_{22}$ represents $O^-$, then r represents zero;
if K or P or M represents —N—($C_1$-$C_4$)alkyl $X^-$, then $R_{23}$ or $R_{24}$ may be other than a hydrogen atom;
if K represents —$NR_{22}(X^-)_r$, then M=P=—CH, —CR;
if M represents —$NR_{22}(X^-)_r$, then K=P=—CH, —CR;
if P represents —$NR_{22}(X^-)_r$, then K=M and represent —CH or —CR;

if Z represents a sulfur atom with $R_{21}$ denoting $C_1$-$C_4$ alkyl, then $R_{20}$ is other than a hydrogen atom;
if Z represents —$NR_{22}$ with $R_{19}$ denoting $C_1$-$C_4$ alkyl, then at least one of the radicals $R_{18}$, $R_{20}$ or $R_{21}$ of the group of structure $G_2$ is other than a $C_1$-$C_4$ alkyl radical;
the symbol J represents:
a) a group of structure $J_1$ below:

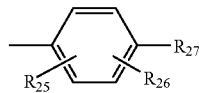

$J_1$ in which structure $J_1$:
$R_{25}$ represents a hydrogen atom, a halogen atom chosen from chlorine, bromine, iodine and fluorine, a $C_1$-$C_4$ alkyl or $C_1$-$C_4$ alkoxy radical, an —OH, —$NO_2$, —$NHR_{28}$, —$NR_{29}R_{30}$ or $C_1$-$C_4$—NHCOalkyl radical, or forms with $R_{26}$ a 5- or 6-membered ring optionally comprising at least one heteroatom chosen from nitrogen, oxygen, and sulfur;
$R_{26}$ represents a hydrogen atom, a halogen atom chosen from chlorine, bromine, iodine and fluorine, a $C_1$-$C_4$ alkyl or $C_1$-$C_4$ alkoxy radical, or forms with $R_{27}$ or $R_{28}$ a 5- or 6-membered ring optionally comprising at least one heteroatom chosen from nitrogen, oxygen, and sulfur;
$R_{27}$ represents a hydrogen atom, an —OH radical, a radical —$NHR_{28}$ or a radical —$NR_{29}R_{30}$;
$R_{28}$ represents a hydrogen atom, a $C_1$-$C_4$ alkyl radical, a $C_1$-$C_4$ monohydroxyalkyl, $C_2$-$C_4$ polyhydroxyalkyl radical or a phenyl radical;
$R_{29}$ and $R_{30}$, which may be identical or different, represent a $C_1$-$C_4$ alkyl radical, a $C_1$-$C_4$ monohydroxyalkyl or $C_2$-$C_4$ polyhydroxyalkyl radical;
(b) a 5- or 6-membered nitrogenous heterocyclic group, which may comprise other heteroatoms and/or carbonyl groups and may be substituted with at least one $C_1$-$C_4$ alkyl, amino or phenyl radicals, such as a group of structure $J_2$ below:

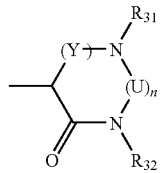

$J_2$ wherein structure $J_2$:
$R_{31}$ and $R_{32}$, which may be identical or different, represent a hydrogen atom, a $C_1$-$C_4$ alkyl radical or a phenyl radical;
Y represents a —CO— radical or a

radical;
n=0 or 1, with, when n represents 1, U denoting a —CO— radical.

In structures (I) to (IV) defined above, the $C_1$-$C_4$ alkyl or alkoxy group may represent methyl, ethyl, butyl, methoxy, or ethoxy.

In certain embodiments, A represents a group chosen from structures $A_1$, $A_4$, $A_7$, $A_{13}$ and $A_{18}$.

Among the compounds of formulae (I) and (III), the following compounds may be used:

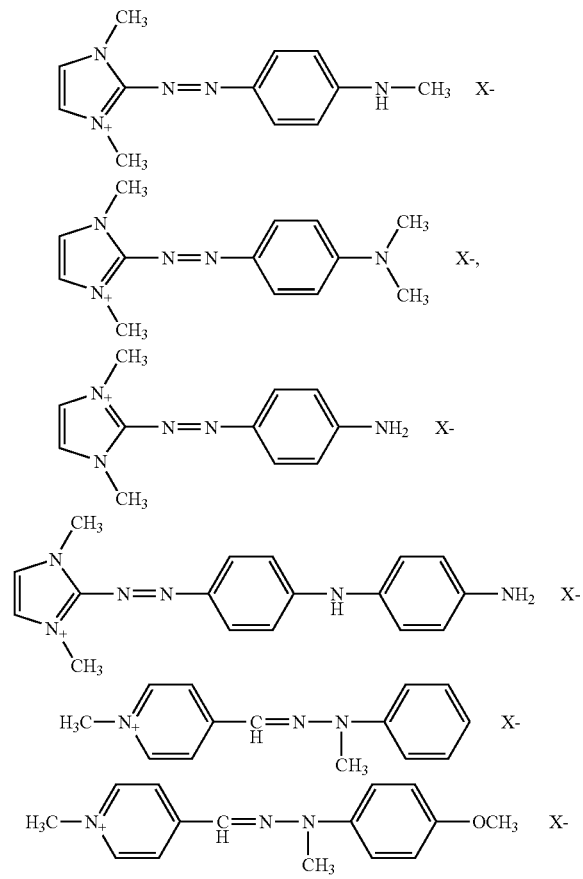

Among the azo direct dyes that may also be mentioned are the following dyes, described in the Color Index International, 3rd edition:
Disperse Red 17
Basic Red 22
Basic Red 76
Basic Yellow 57
Basic Brown 16
Basic Brown 17
Disperse Black 9.

Mention may also be made of 1-(4'-aminodiphenylazo)-2-methyl-4-bis(β-hydroxyethyl)aminobenzene.

Among the quinone direct dyes that may be mentioned are the following dyes:
Disperse Red 15
Solvent Violet β
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are the following compounds:
Basic Blue 17
Basic Red 2.

Among the triarylmethane dyes that may be used according to the disclosure, mention may be made of the following compounds:
Basic Green 1
Basic Violet 3
Basic Violet 14
Basic Blue 7
Basic Blue 26.

Among the indoamine dyes that may be used according to the disclosure, mention may be made of the following compounds:
2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

Among the dyes of tetraazapentamethine type that may be used according to the disclosure, mention may be made of the following compounds given in the table below:

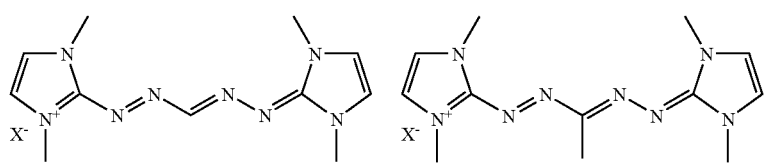

-continued

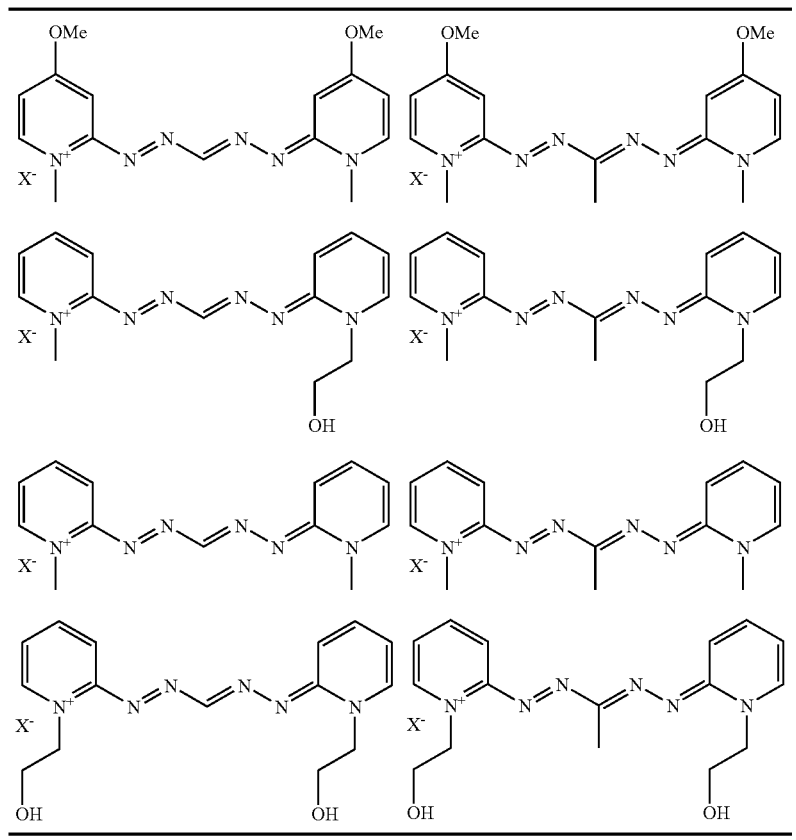

X⁻ represents an anion which may be chosen from chloride, iodide, methyl sulfate, ethyl sulfate, acetate, and perchlorate.

Among the polychromophoric dyes, mention may be made of symmetrical or non-symmetrical azo and/or azomethine (hydrazone) di- or trichromophoric dyes comprising, on the one hand, at least one optionally fused 5- or 6-membered aromatic heterocycle, comprising at least one quaternized nitrogen atom engaged in the said heterocycle and optionally at least one other heteroatom (such as nitrogen, sulfur or oxygen), and, on the other hand, at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group N(R')$_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may be mentioned include 5- or 6-membered rings comprising 1 to 3 nitrogen atoms, such as 1 or 2 nitrogen atoms, one being quaternized; the said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino or amino group substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals, optionally bearing at least one hydroxyl group.

These polychromophores are connected together by means of at least one linker optionally comprising at least one quaternized nitrogen atom that may or may not be engaged in a saturated or unsaturated, optionally aromatic heterocycle.

The linker may be a linear, branched or cyclic $C_1$-$C_{20}$ alkyl chain, optionally interrupted with at least one heteroatom (such as nitrogen or oxygen) and/or with at least one group comprising such a heteroatom (CO or SO$_2$), optionally interrupted with at least one heterocycle that may or may not be fused to a phenyl nucleus and comprising at least one quaternized nitrogen atom engaged in the said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

The bonding between the linker and each chromophore generally takes place via a heteroatom substituent on the phenyl or naphthyl nucleus or via the quaternized nitrogen atom of the cationic heterocycle.

The dye may comprise identical or different chromophores.

As examples of such dyes, reference may be made to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is also possible to use cationic direct dyes mentioned in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or non-cationic linker, and also EP 6 291 333, which describes dyes comprising three chromophores, one of them being an anthraquinone chromophore, to which are attached two chromophores of azo or diazacarbocyanin type or an isomer thereof.

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. It is also possible to use extracts or decoctions comprising these natural dyes and henna-based poultices or extracts.

When they are present, the at least one direct dye may range from 0.0001% to 10% by weight such as from 0.005% to 5% by weight relative to the total weight of the composition.

Composition (C1) may comprise one and/or the other type of dye. It may optionally correspond to two dye compositions, one comprising the oxidation dye(s), the other the direct dye(s).

Composition (C1) may be an aqueous or non-aqueous composition. The term "aqueous composition" means a composition comprising more than 5% by weight of water, such as more than 10% by weight of water or more than 20% by weight of water.

Composition (C1) may be an aqueous composition.

It may optionally comprise an organic solvent. Examples of organic solvents that may be mentioned include $C_2$-$C_4$ linear or branched alkanols, such as ethanol and isopropanol; glycerol; polyols and polyol ethers, for instance 2-butoxyethanol, propylene glycol, dipropylene glycol, propylene glycol monomethyl ether, and diethylene glycol monomethyl ether and monoethyl ether, and also aromatic alcohols such as benzyl alcohol or phenoxyethanol, and mixtures thereof.

The at least one solvent if it is present, may represent a content usually ranging from 1% to 40% by weight such as from 5% to 30% by weight relative to the weight of composition (C1).

The cosmetic composition (C1) may also comprise various adjuvants such as those mentioned in the context of composition (A), for example anionic, cationic, nonionic, amphoteric or zwitterionic surfactants or mixtures thereof, anionic, cationic, nonionic, amphoteric or zwitterionic polymers or mixtures thereof; mineral thickeners, for example fillers such as clays, talc; organic thickeners with, for example, anionic, cationic, nonionic and amphoteric polymeric associative thickeners; antioxidants; penetrants; sequestrants; fragrances; dispersants; film-forming agents; conditioning agents; ceramides; preserving agents; opacifiers.

The above adjuvants are generally present in an amount for each of them ranging from 0.01% to 20% by weight relative to the weight of composition (C1).

The composition may also comprise at least one organic thickener as detailed in the context of composition (A).

According to one embodiment, the organic thickener may be chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropanesulfonic acid crosslinked homopolymers, or from cellulose-based thickeners such as with hydroxyethylcellulose.

The content of at least one organic thickener, if it is present, usually ranges from 0.01% to 20% by weight, such as from 0.1% to 5% by weight, relative to the weight of the composition.

Finally, the process is performed with a composition (B) comprising at least one oxidizing agent.

The at least one oxidizing agent may be chosen from hydrogen peroxide, urea peroxide, alkali metal bromates or ferricyanides, and peroxygenated salts, for instance alkali metal or alkaline-earth metal persulfates, perborates or percarbonates, and also peracids, and precursors thereof.

This oxidizing agent may constitute hydrogen peroxide, for example as an aqueous solution (aqueous hydrogen peroxide solution), the concentration of which may range from 0.1% to 50%, such as ranging from 0.5% to 20% or ranging from 1% to 15% by weight of the oxidizing composition.

As a function of the desired degree of lightening, the oxidizing agent may also comprise an oxidizing agent which may be chosen from peroxygenated salts.

The oxidizing composition may be aqueous or non-aqueous. The term "aqueous composition" means a composition comprising more than 5% by weight of water, such as more than 10% by weight of water or more than 20% by weight of water.

The composition (B) may be an aqueous composition.

It may also comprise at least one organic solvent.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

When they are present, the solvent(s) are in a content usually ranging from 1% to 40% by weight, such as ranging from 5% to 30% by weight, relative to the weight of the oxidizing composition (C).

The oxidizing composition may comprise at least one acidifying agent.

Examples of acidifying agents that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Usually, the pH of the oxidizing composition (B), when it is aqueous, is less than 7.

The oxidizing composition (B) may also comprise other ingredients conventionally used in the field, such as those detailed previously in the context of the anhydrous composition and the dye composition.

Finally, the oxidizing composition is in various forms, for instance a solution, an emulsion or a gel.

According to a variant of the disclosure, a composition obtained by extemporaneous mixing, at the time of use, of the abovementioned anhydrous composition (A) and the abovementioned composition (B) is applied to wet or dry keratin fibers.

In accordance with another variant of the process, compositions (A) and (B) are applied to wet or dry keratin fibers, successively and without intermediate rinsing.

Composition (A) may be applied, then (B).

In these two possible variants, the weight ratio $R_1$ of the amounts of compositions (A)/(B) ranges from 0.1 to 10, such as ranging from 0.3 to 3 or ranging from 0.5 to 1.

According to another variant of the disclosure, a composition obtained by extemporaneous mixing, at the time of use, of the abovementioned anhydrous composition (A), the abovementioned composition (C1) and the abovementioned aqueous oxidizing composition (B) is applied to wet or dry keratin fibers.

In this variant, the weight ratios $R'_1$ of the amounts of compositions (A) and (C1)/(B) and $R'_2$ of the amounts of compositions (A)/(C1) range from 0.1 to 10 such as ranging from 0.3 to 3.

In accordance with another variant of the process, compositions (A), (C1) and (B) are applied to wet or dry keratin fibers, successively and without intermediate rinsing.

The compositions (A), then (C1) and then (B) or (C1), then (A) and then (B) may be applied.

According to another variant, composition (B) and then the mixture resulting from compositions (A) and (C1) may also be applied successively and without intermediate rinsing.

In these last two possible variants, the weight ratios $R'_1$ of the amounts of compositions (A) and (C1)/(B) and $R'_2$ of the amounts of compositions (A)/(C1) may range from 0.1 to 10 such as ranging from 0.3 to 3.

In addition, independently of the variant used, the mixture present on the fibers (resulting either from the extemporaneous mixing of compositions (A), (B) and (C1) when it is present or from their successive application) is left in place for a time generally of the order of 1 minute to 1 hour such as from 5 minutes to 30 minutes.

The temperature during the process is conventionally between room temperature (from 15 to 25° C.) and 80° C. such as between room temperature and 60° C.

After the treatment, the human keratin fibers are optionally rinsed with water, optionally washed with a shampoo followed by rinsing with water, and are then dried or left to dry.

It is pointed out that if the composition applied to the hair (comprising compositions (A), (B) and (C1) when it is present) comprises aqueous ammonia or a salt thereof, its content may be less than or equal to 0.03% by weight of the final composition (expressed as $NH_3$) such as less than or equal to 0.01% by weight relative to the final composition. It is indicated that the final composition results from the mixing of compositions (A), (B) and (C1) when it is present; this mixing being performed either before application to the keratin fibers (extemporaneous preparation) or directly on the keratin fibers (successive applications with or without pre-mixing and without intermediate rinsing). For example, if the composition comprises aqueous ammonia or a salt thereof, then the amount of basifying agent(s) is greater than that of the aqueous ammonia (expressed as $NH_3$).

However, for example compositions (A), (B) and (C1) when it is present do not comprise aqueous ammonia.

According to one variant, the composition according to the disclosure obtained after mixing together the compositions (A), (B) and (C1) described previously is such that, after mixing, the amount of fatty substance is greater than 20% by weight, such as greater than 25% by weight or greater than 30% by weight.

Finally, the disclosure relates to a multi-compartment device comprising, in a first compartment, an anhydrous cosmetic composition (A) comprising at least one fatty substance, at least one surfactant, monoethanolamine and at least one basic amino acid as described previously, and, in a second compartment, a composition (B) comprising at least one oxidizing agent as described previously.

Another multi-compartment device according to the disclosure comprises, in a first compartment, an anhydrous cosmetic composition (A) comprising at least one fatty substance, at least one surfactant, monoethanolamine, and at least one basic amino acid, a composition (C1) comprising at least one oxidation dye and/or direct dye and an aqueous composition (B) comprising at least one oxidizing agent.

The examples that follow serve to illustrate the disclosure without, however, being limiting in nature.

EXAMPLE 1

The following compositions were prepared (unless otherwise indicated, the amounts were expressed in g %):

Composition A

|  | C1 | C2 |
|---|---|---|
| Liquid jojoba wax | 71 | 0 |
| Liquid petroleum jelly | 0 | 71 |
| Oxyethylenated (4 EO) sorbitan monolaurate | 19.5 | 19.5 |
| Pure monoethanolamine | 2.5 | 2.5 |
| Arginine | 7 | 7 |

At the time of use, each composition was mixed weight for weight with an aqueous oxidizing composition comprising hydrogen peroxide as a 20-volumes solution (6% by weight of hydrogen peroxide).

The pH of the resulting mixtures was 10.1±0.1.

Each mixture were then applied to a natural chestnut-brown lock (tone depth 5). The "mixture/lock" bath ratio was 10/1 (g/g).

The leave-on time was 30 minutes at room temperature.

After this time, the locks were rinsed, and then washed with Elvive multivitamin shampoo and dried.

In parallel, a prior art formula based on aqueous ammonia was prepared:

| | |
|---|---|
| Oleyl alcohol polyglycerolated with 2 mol of glycerol | 4 |
| Oleyl alcohol polyglycerolated with 4 mol of glycerol | 5.69 AM |
| Oleic acid | 3 |
| Oleylamine with 2 mol of ethylene oxide, sold under the trade name Ethomeen O12 by the company Akzo | 7 |
| Dimethylaminopropyl laurylaminosuccinamate, sodium salt, at 55% AM | 3.0 AM |
| Oleyl alcohol | 5 |
| Oleic acid diethanolamide | 12 |
| Ethyl alcohol | 7 |
| Propylene glycol | 3.5 |
| Dipropylene glycol | 0.5 |
| Propylene glycol monomethyl ether | 9 |
| Ammonium acetate | 0.8 |
| 20% aqueous ammonia | 10 |
| Demineralized water | qs 100 g |

The percentages were expressed in grams.

AM means that the amount was indicated as grams of active material.

The process was performed with this composition as for the preceding compositions.

It was found that compositions C1 and C2 according to the disclosure have no aggressive odor, unlike the comparative composition, and made it possible to obtain lightening equivalent to that of the comparative composition.

EXAMPLE 2

The following compositions were prepared (unless otherwise indicated, the amounts were expressed in g %):

Composition A

| | |
|---|---|
| Oxyethylenated (4 EO) sorbitan monolaurate | 21.67 |
| Fumed silica of hydrophobic nature | 11.11 |
| Pure monoethanolamine | 2.89 |
| Arginine | 7.00 |
| Liquid petroleum jelly | qs 100 |

Composition B1

| | |
|---|---|
| para-Phenylenediamine | 6.55 |
| Resorcinol | 4.95 |
| 2-Methylresorcinol | 1.86 |
| 1-β-Hydroxyethyloxy-2,4-diaminobenzene dihydrochloride | 0.15 |
| Sodium metabisulfite powder | 0.45 |
| Erythorbic acid | 0.31 |
| Water | qs 100 |

At the time of use, the following were mixed together:
10 parts by weight of composition A,
4 parts by weight of composition B1 with
15 parts by weight of Platinium international 20-volumes oxidizing agent (amount of hydrogen peroxide: 6% by weight).

Each mixture was then applied to a lock of natural hair comprising 90% grey hairs (NG) and to a lock of permanent-waved hair comprising 90% grey hairs (PWG).

The "mixture/lock" bath ratio was, respectively, 10/1 (g/g).

The leave-on time was 30 minutes at 27° C.

After this time, the locks were rinsed, and then washed with Elvive multivitamin shampoo, and dried.

The composition of the disclosure produced a powerful and sparingly selective matte result.

What is claimed is:

1. A process for lightening or dyeing human keratin fibers, comprising applying to the keratin fibers:
   a) at least one anhydrous composition (A) comprising at least one fatty substance, at least one surfactant, monoethanolamine, and at least one basic amino acid; and
   b) at least one aqueous composition (B) comprising at least one oxidizing agent.

2. The process according to claim 1, further comprising applying to the keratin fibers at least one composition (C1) comprising at least one oxidation dye and/or at least one direct dye.

3. The process according to claim 1, wherein the at least one fatty substance is chosen from $C_6$-$C_{16}$ lower alkanes, non-silicone oils of animal, plant, mineral or synthetic origin, fatty alcohols, fatty acids, esters of fatty acids and/or of fatty alcohols, non-silicone waxes, and silicones, and mixtures thereof.

4. The process according to claim 3, wherein the at least one fatty substance is chosen from $C_6$-$C_{16}$ lower alkanes, non-silicone oils of plant, mineral or synthetic origin, fatty alcohols, and esters of fatty acids and/or of fatty alcohols, and mixtures thereof.

5. The process according to claim 1, wherein the at least one fatty substance is chosen from liquid and pasty compounds.

6. The process according to claim 1, wherein the at least one fatty substance is chosen from compounds that are liquid at room temperature and at atmospheric pressure.

7. The process according to claim 1, wherein the at least one fatty substance is present in the at least one anhydrous composition (A) in an amount ranging from 10% to 99% by weight, relative to the weight of the at least one anhydrous composition (A).

8. The process according to claim 7, wherein the at least one fatty substance is present in the at least one anhydrous composition (A) in an amount ranging from 20% to 90% by weight, relative to the weight of the at least one anhydrous composition (A).

9. The process according to claim 8, wherein the at least one fatty substance is present in the at least one anhydrous composition (A) in an amount ranging from 25% to 80% by weight, relative to the weight of the at least one anhydrous composition (A).

10. The process according to claim 1, wherein the at least one surfactant is at least one nonionic surfactant.

11. The process according to claim 10, wherein the at least one nonionic surfactant is chosen from monooxyalkylenated, polyoxyalkylenated, monoglycerolated, and polyglycerolated nonionic surfactants.

12. The process according to claim 1, wherein the at least one surfactant is present in an amount ranging from 0.1% to 50% by weight, relative to the weight of the at least one anhydrous composition (A).

13. The process according to claim 12, wherein the at least one surfactant is present in an amount ranging from 0.5% to 30% by weight, relative to the weight of the at least one anhydrous composition (A).

14. The process according to claim 1, wherein the at least one basic amino acid is chosen from the compounds of formula (I):

wherein R represents a group chosen from:

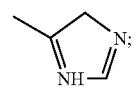

—$(CH_2)_3NH_2$;
—$(CH_2)_2NH_2$;
—$(CH_2)_2NHCONH_2$; and

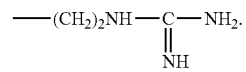

15. The process according to claim 14, wherein the at least one basic amino acid is chosen from arginine, histidine, and lysine, and mixtures thereof.

16. The process according to claim 1, wherein monoethanolamine is present in an amount ranging from 0.1% to 40% by weight, relative to the weight of the at least one composition (A).

17. The process according to claim 16, wherein monoethanolamine is present in an amount ranging from 0.5% to 20% by weight, relative to the weight of the at least one composition (A).

18. The process according to claim 1, wherein the at least one basic amino acid is present in an amount ranging from 0.1% to 40% by weight, relative to the weight of the at least one anhydrous composition (A).

19. The process according to claim 18, wherein the at least one basic amino acid is present in an amount ranging from 0.5% to 20% by weight, relative to the weight of the at least one anhydrous composition (A).

20. The process according to claim 1, wherein monoethanolamine and the at least one basic amino acid are present at a weight ratio ranging from 0.1 to 10.

21. The process according to claim 20, wherein the at least one monoethanolamine and the at least one basic amino acid are present at a weight ratio ranging from 0.3 to 10.

22. The process according to claim 21, wherein the monoethanolamine and the at least one basic amino acid are present at a weight ratio ranging from 1 to 5.

23. The process according to claim 1, wherein a composition obtained by extemporaneous mixing, at the time of use, of the at least one composition (A) and at least one composition (B) and optionally (C1) is applied to keratin fibers.

24. A process according to claim 1, wherein the at least one composition (A) and the at least one composition (B) and the at least one composition (C1) are applied to keratin fibers, successively and without intermediate rinsing.

25. A multi-compartment device according to claim 1, comprising, in a first compartment, at least one anhydrous composition (A) and, in another compartment, at least one composition (B) comprising at least one oxidizing agent.

26. A multi-compartment device according to claim 1, comprising, in a first compartment, at least one anhydrous composition (A), in another compartment, at least one composition (B), and, in a third compartment, at least one aqueous composition (C1) comprising at least one oxidizing agent.

* * * * *